United States Patent
Olah et al.

(10) Patent No.: US 8,791,166 B2
(45) Date of Patent: Jul. 29, 2014

(54) PRODUCING METHANOL AND ITS PRODUCTS EXCLUSIVELY FROM GEOTHERMAL SOURCES AND THEIR ENERGY

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 481 days.

(21) Appl. No.: 12/501,157

(22) Filed: Jul. 10, 2009

(65) Prior Publication Data

US 2010/0022671 A1    Jan. 28, 2010

Related U.S. Application Data

(60) Provisional application No. 61/083,392, filed on Jul. 24, 2008.

(51) Int. Cl.
*C07C 27/06* (2006.01)
*C25B 3/00* (2006.01)
*C07C 4/06* (2006.01)

(52) U.S. Cl.
USPC ........... 518/704; 518/700; 518/713; 518/714; 518/726; 568/864; 568/885; 205/450; 585/653

(58) Field of Classification Search
None
See application file for complete search history.

(56) References Cited

U.S. PATENT DOCUMENTS

| 4,085,795 A | * | 4/1978 | Gill ............................ 165/45 |
| 4,927,856 A | * | 5/1990 | Elion .......................... 518/702 |
| 5,928,806 A | | 7/1999 | Olah et al. .................. 429/13 |
| 2006/0235091 A1 | | 10/2006 | Olah et al. .................. 518/726 |

FOREIGN PATENT DOCUMENTS

WO    WO2008021700 A1    2/2008

OTHER PUBLICATIONS

International Search Report and Written Opinion of the International Searching Authority, Application No. PCT/US2009/050199, Jan. 26, 2010.
Ingvar B. Fridleifsson, "Geothermal Energy for the Benefit of the People," Renewable and Sustainable Energy Reviews 5, pp. 299-312 (2001).
Supplementary European Search Report, (Appln. No. 09800788.3) PCT/US2009050199, dated Jan. 1, 2013.

* cited by examiner

*Primary Examiner* — Yate K Cutliff
(74) *Attorney, Agent, or Firm* — Winston & Strawn LLP

(57) ABSTRACT

The invention provides a method for producing methanol and its products exclusively from a geothermal source as the sole source material also using the needed energy from the geothermal energy source. The method includes separating or isolating carbon dioxide accompanying hot water or steam of the source, generating hydrogen from the water and subsequently preparing methanol from the carbon dioxide and hydrogen. The methanol can be further converted into dimethyl ether or other products.

14 Claims, No Drawings

PRODUCING METHANOL AND ITS PRODUCTS EXCLUSIVELY FROM GEOTHERMAL SOURCES AND THEIR ENERGY

This application claims the benefit of application No. 61/083,392 filed Jul. 24, 2008, the entire content of which is expressly incorporated herein by reference thereto.

FIELD OF THE INVENTION

The invention relates to the production of methanol, dimethyl ether and derived synthetic hydrocarbons exclusively from geothermal sources and their energy.

BACKGROUND OF THE INVENTION

Fossil fuels are major energy sources today and also serve as raw materials for various hydrocarbons and their derived products. However, fossil fuel reserves are on the decline.

An alternative to fossil fuels are geothermal energy sources. Geothermal energy sources provide hot water and steam and are increasingly used as alternative energy sources for generating electrical energy as well as for heating purposes. Hot water and steam are available as natural sources (geysers) or can be obtained by tapping (drilling) into suitable geological formations and pumping (passing) external water through them.

Geothermal energy sources and related geothermal wells usually also discharge carbon dioxide accompanying hot water or steam. Geothermal energy plants release carbon dioxide as a by-product in amounts from 2 to 40%, which is generally clean or can be readily purified by known methods. It has been until now usually vented into the atmosphere. Carbon dioxide can however be readily separated and used as a carbon source for the production of methanol and/or dimethyl ether, derived synthetic hydrocarbons and their products. The required hydrogen is generated from cleavage (electrolytic, thermal) of water using the heat or electricity produced by the same geothermal energy source.

SUMMARY OF THE INVENTION

The invention provides for a method for producing methanol and its products exclusively from geothermal sources and their energy. The method comprises using the hot water or steam as well as accompanying carbon dioxide of the geothermal source, generating hydrogen from the water as well as isolating accompanying carbon dioxide and converting them to methanol and its products. The carbon dioxide and water derived hydrogen are obtained exclusively from the geothermal source as is the energy needed for the process.

In particular, the method comprises obtaining carbon dioxide and water or steam solely from the geothermal source, generating hydrogen from the water or steam, isolating the carbon dioxide accompanying the water or steam of the source, and converting the isolated carbon dioxide and generated hydrogen to methanol.

Accompanying carbon dioxide is isolated by absorption or adsorption on a suitable absorbent such as polyamino containing polymer deposited on a nano-structured high surface area support. The polyamino containing polymer is a polyethyleneimine and the support is fused nano-structured silica or alumina.

Hydrogen is generated from water by electrolysis, catalytic thermal cleavage or any other method with needed energy also provided by the geothermal source. The methanol is produced from the carbon dioxide and hydrogen by any known method using energy provided by the geothermal source.

In one embodiment, the carbon dioxide is converted to methanol by any hydrogenative method. Further, methanol can be produced under conditions sufficient to form first carbon monoxide, the carbon monoxide is then reacted with methanol under conditions sufficient to obtain methyl formate and the methyl formate is catalytically hydrogenated under conditions sufficient to produce exclusively methanol.

In a further embodiment, the methanol can be further converted to produce dimethyl ether, which can be reacted in the presence of an acidic-basic or zeolytic catalyst under conditions sufficient to form ethylene and/or propylene. The ethylene or propylene are further converted under conditions sufficient to produce synthetic hydrocarbons, derived chemicals, polymers and products derived therefrom.

DETAILED DESCRIPTION OF THE PREFERRED EMBODIMENTS

The invention relates to the use of geothermal energy sources providing accompanying carbon dioxide and water derived hydrogen as well as needed energy to produce methanol and compounds derived from methanol such as dimethyl ether, which can be used for energy storage and transportation, production of transportation fuels and derived synthetic hydrocarbon products.

The use of geothermal energy sources as the sole source for the conversion of accompanying carbon dioxide and water derived hydrogen to methanol or dimethyl ether using the needed energy provided by the source provides unique and significant advantages by enabling the exclusive utilization of a geothermal energy source to produce essential fuels and hydrocarbon products. It thus provides a basis for fuels and materials needed to replace increasingly diminishing reserves of fossil fuels.

Accompanying carbon dioxide can be isolated from a geothermal energy source by any suitable means. An efficient process for capturing and reversibly adsorbing carbon dioxide gas includes without limitation a polyamino polymer (e.g., polyethylenimine) deposited on a nano-structured high surface area support (e.g., fused silica or alumina), as taught by our International application no. PCT/US07/74615 filed Jul. 7, 2007, the entire content of each of which are incorporated herein by reference thereto. Generally, the supported amine sorbents comprise an amine or an amine/polyol composition deposited on a nano-structured support, which provide structural integrity and increased $CO_2$ absorption capacity. The support for the amine and amine/polyol compositions is composed of a nano-structured solid. The nano-structured support can have a primary particle size less than about 100 nm, and can be nanosilica, fumed or precipitated oxide, calcium silicate, carbon nanotube, or a mixture thereof. The amine can be a primary, secondary, or tertiary amine or alkanolamine, aromatic amine, mixed amines or combinations thereof. In an example, the amine is present in an amount of about 25% to 75% by weight of the sorbent. The polyol can be selected from, for example, glycerol, oligomers of ethylene glycol, polyethylene glycol, polyethylene oxides, and ethers, modifications and mixtures thereof, and can be provided in an amount up to about 25% by weight of the sorbent. After carbon dioxide is captured, it can be released readily through heating and/or reduced pressure for use in the processes described herein.

Water or steam is gained from the geothermal energy source by any suitable means. As clean water is frequently not otherwise available in many locations or may need extensive purification (e.g., by distillation) before it can be used for generating hydrogen, water or steam obtained from a geothermal source is most suitable to be used as a hydrogen source. Hydrogen can be generated from the geothermal water or steam by any suitable means including electrolysis or other means of catalytic or thermal cleavage.

Geothermal energy sources also provide an alternate source of energy to produce electricity or to be used as heat energy, which can be used by any suitable means. They can be also utilized in the process of isolating carbon dioxide from the source and generating hydrogen from the water. Electrical energy can be generated by passing steam through turbines or by any other means utilizing steam or hot water to generate electricity or heat energy.

Carbon dioxide and water derived hydrogen can be used to produce methanol or dimethyl ether according to the processes described in U.S. Pat. No. 5,928,806 and co-pending U.S. patent application Ser. No. 11/402,050 filed Apr. 12, 2006 (publication no US2006/0235091-A1), the entire content of each of which are incorporated herein by reference thereto. U.S. Pat. No. 5,928,806 describes a method of reducing carbon dioxide and water to form oxygenated hydrocarbons such as methyl alcohol, methyl formate, formaldehyde or formic acid by, for example, providing carbon dioxide, water and electrical energy to a reduction zone such that the carbon dioxide and water react to form oxygen and an oxygenated hydrocarbon or a mixture of oxygenated hydrocarbons. U.S. patent application Ser. No. 11/402,050 provides methods for converting carbon dioxide to methanol by catalytic hydrogenation and discloses that hydrogen used in the catalytic hydrogenation can be obtained from any suitable source, including electrolysis of water. U.S. patent application Ser. No. 11/402,050 discloses reducing carbon dioxide to produce a reaction mixture containing formic acid with concomitant formation of formaldehyde and smaller amounts of methanol. It is followed by a treatment to convert the formaldehyde and formic acid to methanol. Besides using Canizzaro-Tischenko type chemistry to convert formaldehyde to methanol, the amount of methanol produced can be increased by reacting the formaldehyde with formic acid (as a hydrogen source) to synthesize methanol. Alternatively, formic acid can be reacted with methanol to form methyl formate, which upon catalytic hydrogenation will give twice the amount of methanol. Through another route, carbon dioxide can be used to generate carbon monoxide through a high temperature reaction with carbon and then reacting the carbon monoxide so produced with methanol to form methyl formate, followed by catalytic hydrogenation to methanol.

Methanol or dimethyl ether produced according to the invention are also convenient to store and transport energy. Methanol is also an excellent transportation fuel and can be easily treated to produce synthetic hydrocarbons and derived materials. It can also be converted to dimethyl ether, (which is produced by dehydration of methanol) or to dimethyl carbonate. Dimethyl carbonate can be produced by oxidative carbonylation of methanol.

Methanol or dimethyl ether can be converted in the presence of an acidic-basic or zeolitic catalyst to produce ethylene and/or propylene, which are useful to produce polymers, and as feedstock for other synthetic hydrocarbons, derived materials and chemicals including transportation fuels. For example, ethylene and propylene can be hydrated to form ethanol and propanol, respectively, they can be converted to higher olefins, polyolefins, varied synthetic hydrocarbons, or aromatic compounds, as well as products produced from these compounds. Thus, methanol, dimethyl ether, and synthetic hydrocarbon products and compounds derived from them are useful as convenient and safely storable energy sources and fuels, as well as useful starting materials for various chemicals, synthetic hydrocarbons and related products.

Methanol can also be used as a food source for single-cell organisms or microorganisms to produce proteins, e.g., single cell proteins, in aqueous media in the presence of nitrogen-containing nutrient salts, by utilizing nitrogen from the air. Thus, the invention also provides a method for producing nitrogen-containing alimentary products such as proteins by utilizing carbon dioxide and water. In this embodiment, the atmospheric air is used not only as a renewable carbon source (i.e., carbon dioxide) and a source of hydrogen (derived from the air's moisture content) but also as a source of nitrogen for producing nitrogen-containing proteins. Single cell proteins thus produced can be used for any desired purpose including human or animal alimentation.

EXAMPLES

The following examples are provided to illustrate preferred embodiments of the invention.

Example 1

Accompanying carbon dioxide is separated by any known method from the geothermal source. Geothermal energy sources can utilize either water (steam) of natural origin (geyser) or use external water injected into a suitable geological formation to be naturally heated and subsequently recovered.

Example 2

Water from a geothermal source is utilized to generate hydrogen using any known method such as electrolysis or any other method of cleavage. Hydrogen is utilized for the chemical conversion of carbon dioxide to methanol by any known method.

Example 3

The energy needed for the processes in Examples 1 and 2 is derived by converting the heat energy of a geothermal energy source to electrical energy by any known process.

The invention is not to be limited in scope by its specific embodiments described herein. Various modifications within the spirit and scope of the invention in addition to those described herein will become apparent to those skilled in the art from the foregoing description. Such modifications are intended to fall within the scope of the invention described herein.

What is claimed is:

1. A method for producing methanol from a geothermal energy source, which comprises obtaining water or steam from the source; generating hydrogen from the water or steam; isolating carbon dioxide from the source by sorption on suitable absorbent material; and converting the isolated carbon dioxide and generated hydrogen to methanol; wherein the isolated carbon dioxide and generated hydrogen are obtained solely from the geothermal source and the methanol is produced exclusively from the isolated carbon dioxide and hydrogen generated and the geothermal source provides all energy necessary for the production of methanol.

2. The method of claim 1, wherein the absorbent material is a polyamino containing polymer deposited on a nano-structured high surface area support.

3. The method of claim 2, wherein the polyamino containing polymer is a polyethyleneimine and the support is fused silica or alumina.

4. The method of claim 1, wherein the hydrogen is generated by electrolysis or catalytic or thermal cleavage.

5. The method of claim 1, which comprises reducing the carbon dioxide with hydrogen under conditions sufficient to produce a reaction mixture containing formic acid with concomitant formation of formaldehyde and smaller amounts of methanol; followed by converting the formaldehyde and formic acid to exclusively form methanol.

6. The method of claim 1, wherein the isolated carbon dioxide and generated hydrogen are converted to methanol by generating carbon monoxide from the carbon dioxide through a high temperature reaction, then reacting the carbon monoxide so produced with methanol to form methyl formate, followed by catalytic hydrogenation of the methyl formate with the generated hydrogen to form the methanol.

7. A method for producing dimethyl ether from a geothermal energy source, which comprises obtaining water or steam from the source; generating hydrogen from the water or steam; isolating carbon dioxide from the source by sorption on suitable absorbent material; converting the isolated carbon dioxide and generated hydrogen to methanol; and converting the methanol under conditions sufficient to produce dimethyl ether, wherein the isolated carbon dioxide and generated hydrogen are obtained solely from the geothermal source and the methanol is produced exclusively from the isolated carbon dioxide and hydrogen generated and the geothermal source provides all energy necessary for the production of methanol.

8. The method of claim 7, wherein the absorbent material is a polyamino containing polymer deposited on a nano-structured high surface area support.

9. The method of claim 8, wherein the polyamino containing polymer is a polyethyleneimine and the support is fused silica or alumina.

10. The method of claim 7, wherein the hydrogen is generated by electrolysis or catalytic or thermal cleavage of water.

11. The method of claim 10, which comprises reducing the carbon dioxide with the hydrogen under conditions sufficient to produce a reaction mixture containing formic acid with concomitant formation of formaldehyde and smaller amounts of methanol; followed by converting the formaldehyde and formic acid to exclusively form methanol.

12. The method of claim 7, wherein the isolated carbon dioxide and generated hydrogen are converted to methanol by generating carbon monoxide from the carbon dioxide through a high temperature reaction, then reacting the carbon monoxide so produced with methanol to form methyl formate, followed by catalytic hydrogenation of the methyl formate with the generated hydrogen to form the methanol.

13. The method of claim 7, which further comprises reacting the produced methanol or dimethyl ether in the presence of a bifunctional acidic-basic or zeolytic catalyst under conditions sufficient to form ethylene or propylene.

14. The method of claim 13, which further comprises converting the ethylene or propylene under conditions sufficient to produce synthetic hydrocarbons, derived chemicals, polymers or products derived from them.

* * * * *